(12) United States Patent
White

(10) Patent No.: US 7,984,638 B2
(45) Date of Patent: Jul. 26, 2011

(54) GAS CHROMATOGRAPH OVEN

(75) Inventor: Robert L. White, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 349 days.

(21) Appl. No.: 12/167,483

(22) Filed: Jul. 3, 2008

(65) Prior Publication Data

US 2010/0000291 A1    Jan. 7, 2010

(51) Int. Cl.
*G01N 30/04* (2006.01)
(52) U.S. Cl. ............. 73/23.41; 73/23.35; 95/87; 96/101
(58) Field of Classification Search .............. 73/23.35, 73/23.41; 95/82, 87, 89; 96/101, 103, 105
See application file for complete search history.

(56) References Cited

U.S. PATENT DOCUMENTS

| | | | | |
|---|---|---|---|---|
| 3,290,482 A * | 12/1966 | Dodd et al. | ............... | 219/201 |
| 4,045,998 A * | 9/1977 | Ford | ............... | 73/23.24 |
| 4,181,613 A * | 1/1980 | Welsh et al. | ............... | 210/179 |
| 4,771,628 A * | 9/1988 | Sisti et al. | ............... | 73/23.25 |
| 4,948,389 A * | 8/1990 | Klein et al. | ............... | 95/18 |
| 5,032,151 A * | 7/1991 | Klein et al. | ............... | 95/17 |
| 5,311,445 A | 5/1994 | White | | |
| 5,665,314 A * | 9/1997 | Berger et al. | ............... | 422/89 |
| 5,808,178 A | 9/1998 | Rounbehler et al. | | |
| 5,830,321 A | 11/1998 | Lindsay et al. | | |
| 5,938,817 A | 8/1999 | Shibamoto et al. | | |
| 6,248,158 B1 * | 6/2001 | Abdel-Rahman et al. | ...... | 96/101 |
| 6,354,136 B1 | 3/2002 | Bremer et al. | | |
| 6,920,777 B1 | 7/2005 | Miller | | |
| 7,238,321 B2 | 7/2007 | Wittwer et al. | | |
| 2003/0072690 A1 * | 4/2003 | Royer et al. | ............... | 422/131 |

OTHER PUBLICATIONS

International Search Report dated Dec. 31, 2008.

* cited by examiner

*Primary Examiner* — Daniel S Larkin
(74) *Attorney, Agent, or Firm* — Dunlap Codding, P.C.

(57) ABSTRACT

A gas chromatograph oven including a housing, a capillary tube and a thermal control assembly. The housing defining a capillary tube receiving space and having at least one outlet port to permit the passage of a fluid from the capillary tube receiving space of the housing. The capillary tube is positioned in the capillary tube receiving space of the housing and has a gas inlet end connectable to a gas injector and a gas detector end connectable to a gas detector. The thermal control assembly is in fluid communication with the capillary tube receiving space of the housing and is connectable to a source of a temperature regulating fluid.

21 Claims, 8 Drawing Sheets

GAS CHROMATOGRAPH OVEN

BACKGROUND OF THE INVENTION

1. Field of the Invention

The present invention relates in general to a gas chromatograph oven and, more particularly, but not by way of limitation, to a gas chromatograph oven which allows for fast and repetitive sampling of injections.

2. Brief Description of Related Art

Gas chromatography is a means of separating volatile mixture components by selective transport through a column. The column contains a substance called a stationary phase which has a different affinity for each of the mixture components passing through the column. As a result of component interactions with the stationary phase, some are retained on the column longer than others. In a successful separation, components leave the column one at a time. The stationary phase affinity for volatile mixture components is temperature dependent. A common technique used to enhance separation efficiency is to change the stationary phase temperature during the separation. In order to accomplish this, gas chromatograph instruments employ an oven with precise and reproducible temperature control. Highly efficient separations can be achieved in short times by using narrow bore capillary columns and high column heating rates (>1° C./second). Ovens in commercial instruments vary in size, but typically they contain a heating element and fan mounted on an inside wall. The fan circulates the heated air to achieve uniform column heating. After completing a temperature ramp gas chromatographic separation, the oven is typically cooled by opening a door, which allows the hot air to escape. Some ovens can be cooled faster by introducing a coolant such as liquid nitrogen. Faster cooling reduces the time between analyses, which minimizes turnaround times. This is particularly important when gas chromatography is used for process monitoring or for automated analysis of multiple samples with an autosampler.

Gas chromatograph ovens for use in chromatographic analysis have been known for years. Nevertheless, problems related to efficiency and consumption of resources exist. In particular, traditional gas chromatograph ovens are often large devices which require substantial amounts of energy to power. Typically, gas chromatograph ovens include a housing with vents for emitting air, a sealed door, a large fan for circulating air within the housing, and a heating element. These and other moving parts associated with traditional gas chromatograph ovens only serve to increase maintenance costs and process inefficiencies. These detriments also serve to make "fast" chromatography a cumbersome process and also prevent a user from conducting on-site gas chromatography analyses because the size of standard chromatograph ovens make them unsuitable for use in portable devices. Finally, rapid cooling, and thus rapid thermal cycling, is difficult with traditional gas chromatograph ovens due to large amounts of liquid nitrogen being required, which increases the cost of operating the oven.

Thus, a need exists for a gas chromatograph oven which reduces the need for maintenance of the same, enables rapid thermal cycling, and provides for efficacious and/or automated analysis of multiple samples. It is to such an apparatus that the present invention is directed.

DETAILED DESCRIPTION OF THE INVENTION

Figure 1:
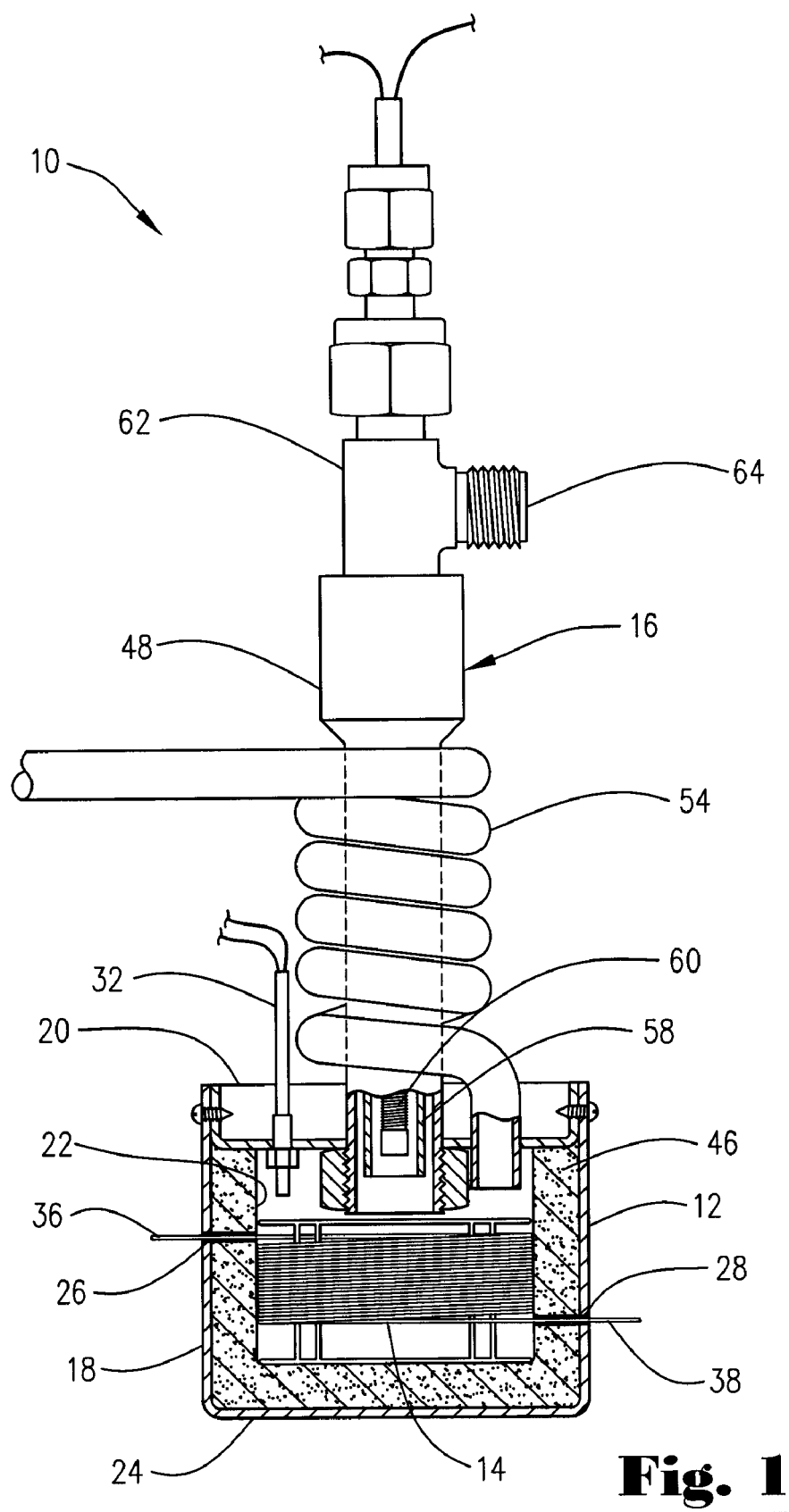
FIG. 1 is a side elevational view, partially in cross-section, of a gas chromatograph oven constructed in accordance with the present invention.
Figure 2:
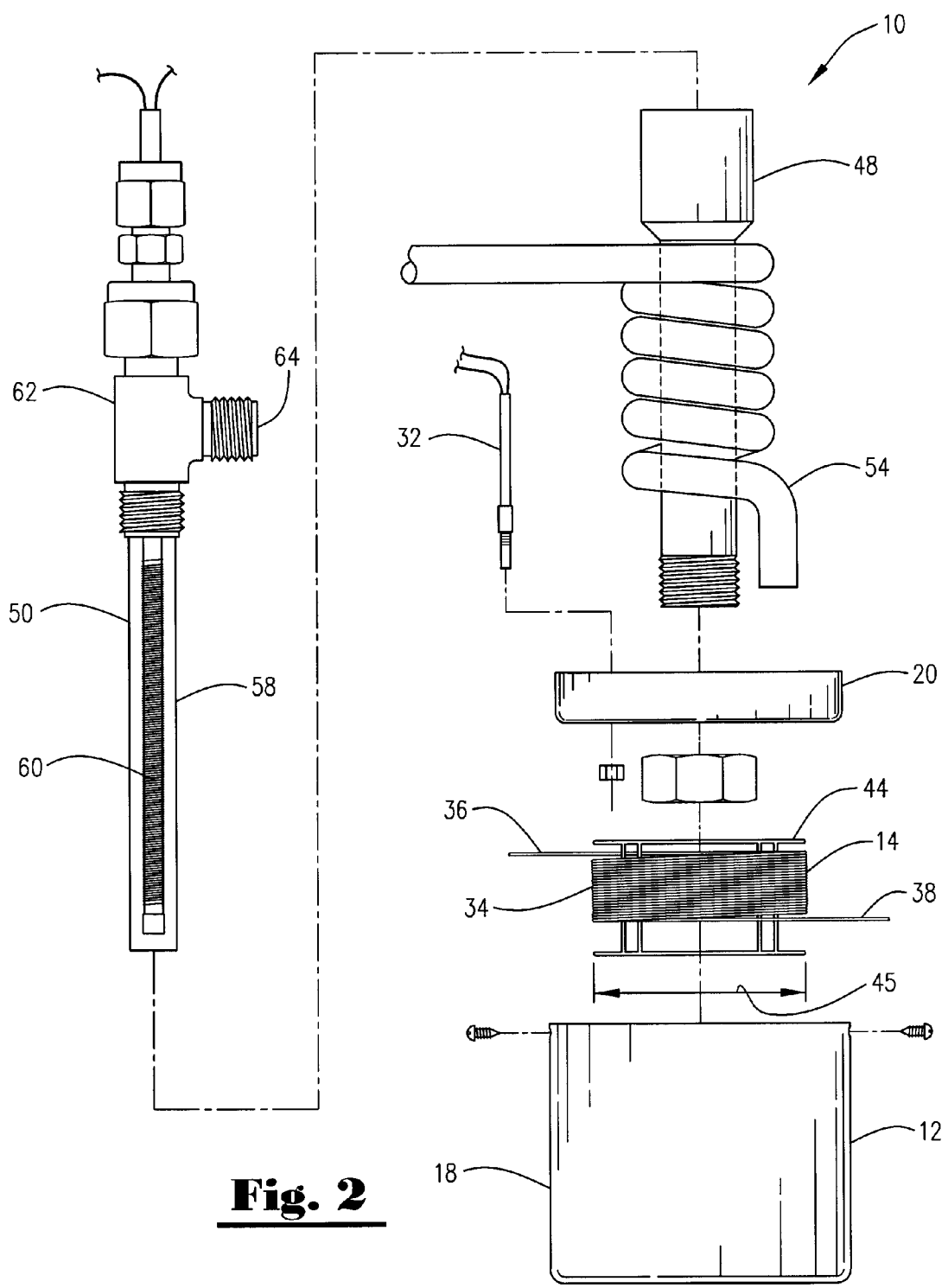
FIG. 2 is an exploded, elevational view of the gas chromatograph oven.

Referring now to the drawings, and to FIGS. 1 and 2 in particular, a gas chromatograph oven 10 constructed in accordance with the present invention is shown as generally including a housing 12, a capillary tube 14 positioned in the housing 12, and a thermal control assembly 16 in fluid communication with the interior of the housing 12.

The housing 12 includes a body member 18 and a cap member 20. The body member 18 and the cap member 20 cooperate to define a capillary tube receiving space 22. The body member 18 may be fabricated from any suitable material, such as a ceramic, aluminum, steel, or brass. The body member 18 is shown as having a substantially cylindrical shape; however, the body member 18 may include any number of geometries such as rectangular, triangular, and polygonal. The body member 18 is sealed on one end with a bottom plate 24. The body member 18 and the bottom plate 24 are preferably fabricated as a unitary member; however, the bottom plate 24 may be formed as a separate member from the body member 18.

The body member 18 includes a gas inlet capillary aperture 26 and a gas detector capillary aperture 28. The gas inlet capillary aperture 26 and the gas detector capillary aperture 28 are sized to receive a portion of the capillary tube 14 in a manner to be discussed below.

The cap member 20 is preferably fabricated from the same material as the body member 18, though other materials may also be utilized. The cap member 20 is releaseably securable to the body member 18. This releaseable securement allows for a user to access the capillary tube receiving space 22 of the housing 12. The cap member 20 may be secured to the body member 18 in any suitable fashion. For example, the cap member 20 may be secured to the body member 18 with threaded fasteners or the cap member 20 and the body member 18 may be provided with corresponding threaded areas. In another embodiment, the cap member 20 may be press fit onto the body member 18.

The cap member 20 may be formed in a variety of shapes. The cap member 20 is shown herein as being shaped to support the thermal control assembly 16 and as having a plurality of outlet ports 30 (FIGS. 3 and 4) which allow for the discharge of a gas and/or a liquid from the capillary tube receiving space 22 of the housing 12. In addition, the cap member 20 may support a thermocouple 32. It will be appreciated, however, that the thermal control assembly 16 and the thermocouple 32 may be supported by the bottom plate 24 of the housing 12. In addition, the outlet ports 30 may be formed in the bottom plate 24. To this end, the primary function of the cap member 20 is to allow access to the capillary tube receiving space 22.

The capillary tube 14 is a length of tubing coiled to form a coiled capillary column 34 which has a gas inlet end 36 and a gas detector end 38. The gas inlet end 36 is connectable to a gas injector 40 (FIG. 4), and the gas detector end 38 is connectable to a gas detector 42 (FIG. 4), such as a mass spectrometer. The coiled column 34 is supported by a frame 44. To reduce the volume of air required to be heated, the capillary column 34 is preferably coiled to a minimum diameter 45. It will be appreciated that capillary tubes are typically formed of a fused silica tubing. It has been found that when using a fused silica tubing, the capillary tube 14 may be generally coiled to have a minimum diameter 45 of about 1.5 inches. However, it should be understood that the capillary tube 14 may be formed of a variety of materials which may dictate the dimensions of the capillary column 34.

The capillary tube 14 is positioned in the body member 18 of the housing 12 with the gas inlet end 36 extending through the gas inlet capillary aperture 26 and the gas outlet end 38 extending through the gas detector capillary aperture 28. The housing 12 preferably is sized so that the housing 12 and the capillary tube 14 are in a non-contact relationship. To reduce the volume of air to be heated and/or cooled about the capillary tube 14 and thus facilitate rapid heating and/or cooling of the capillary tube 14, a layer of insulation 46 may be positioned between the interior surface of the housing 12 and the capillary tube 14. It will be understood that, while only one capillary tube 14 is illustrated, the gas chromatograph oven 10 may employ a plurality of capillary tubes 14.

The thermal control assembly 16 is in fluid communication with the capillary tube receiving space 22 of the housing 12. The thermal control assembly 16 includes a port interface 48 connected to the housing 12, a heating member 50 connectable to a source of temperature regulating fluid 52, such as air, and a cooling port 54 connectable to a source of cooling fluid 56.

The port interface 48 is a conduit connected to the cap member 20 to provide a port into the capillary tube receiving space 22. To this end, it should be appreciated that the port interface 48 may be formed as an integral member with the cap member 20 or may be formed as an integral member with the bottom plate 24 or be a separate member that is connected to the bottom plate 24.

The heating member 50 includes a tube 58 having a heating element 60 positioned therein. The heating element 60 is shown to be an electrical resistive coil wire. The tube 58 may formed of any sufficient heat insulating material, such as quartz or ceramic. The tube 58 and the heating element 60 are supported by a conduit 62 having a fluid inlet 64 which is in fluid communication with the interior of the tube 58 and thus the heating element 60.

To heat the capillary tube receiving space 22 of the housing 12, and in turn heat the capillary tube 14, a temperature regulating fluid, such as air, is passed through the fluid inlet 64 and into the tube 58 where it is caused to be heated by the heating element 60. The heated fluid then passes into the capillary tube receiving space 22 of the housing 12 where the heated fluid circulates about the capillary tube 14. The heated fluid then passes from the housing 12 through the outlet ports 30 of the housing 12.

The cooling port 54 comprises a tube which facilitates the communication of a cooling fluid into capillary tube receiving space 22 of the housing 12. In one embodiment, the cooling port 54 may be coiled around at least a portion of the periphery of the port interface 48. By being positioned in contact with the port interface 48, the cooling port 54 further functions to cool the port interface 48 which can become hot during the heating phase because of its proximity to the heating member 50. To communicate a cooling fluid, the cooling port 54 preferably passes through an aperture associated with either the body member 18 or the cap member 20. By way of a non-limiting example, the cooling liquid utilized may be liquid nitrogen. The use of liquid nitrogen allows for "cryogenic focusing" which enhances the resolution of the acquired chromatographic data.

Figure 3:
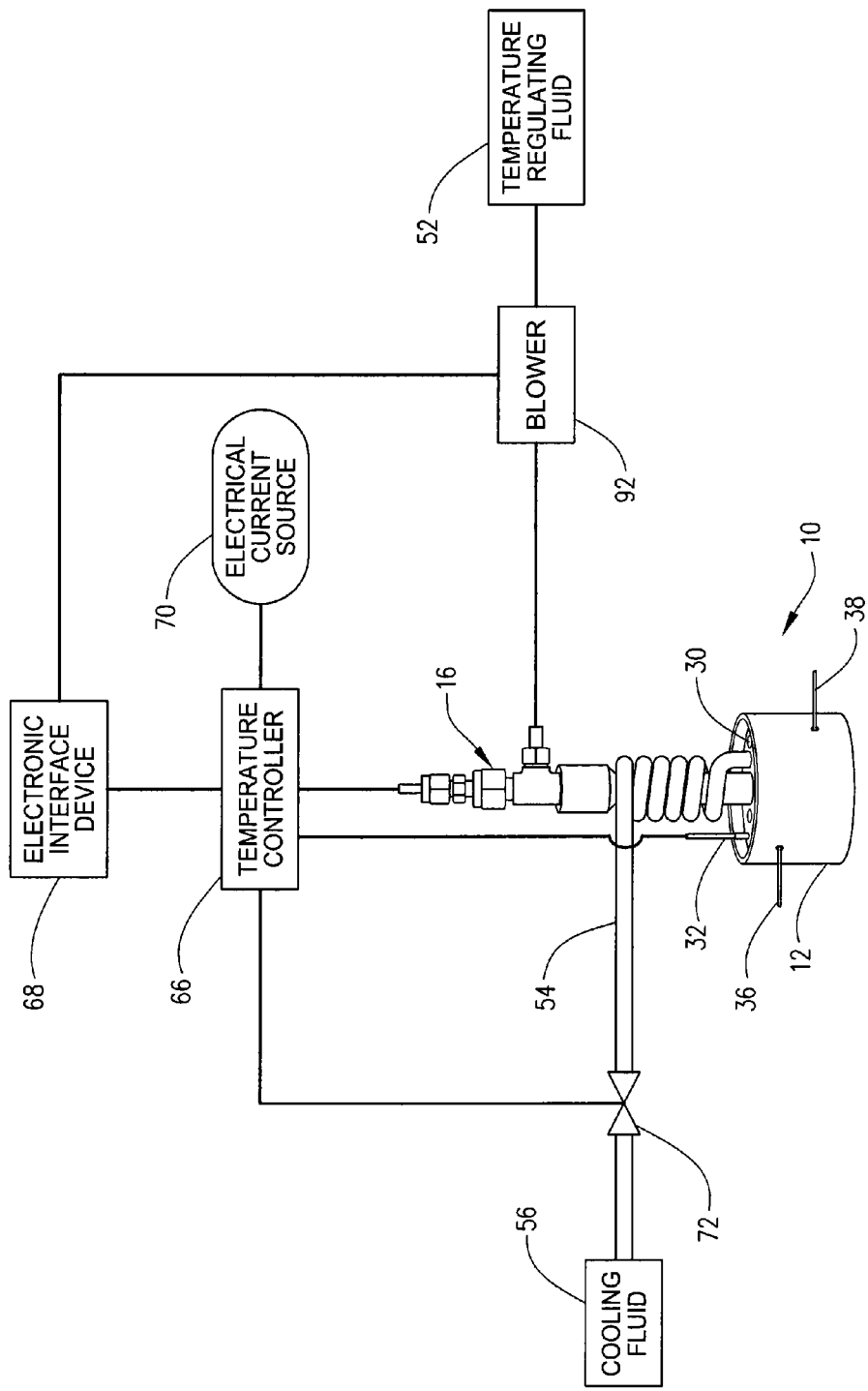
FIG. 3 is a schematic representation of the gas chromatograph oven and associated controls.

Referring now to FIG. 3, a schematic representation of the gas chromatograph oven 10 and associated controls is shown. To control the temperature of the gas chromatograph oven 10, the gas chromatograph oven 10 further includes a temperature controller 66. The temperature controller 66 is associated with an electronic interface device 68 (i.e., a computer, a hand-held electronic device) and the thermocouple 32 to operate the temperature controller 66. The heating element 60 of the thermal control assembly 16 is shown as associated with an electrical current source 70 via the temperature controller 66. The electrical current source 70 may comprise, for example, an electrochemical cell or a standard utility outlet (i.e., 110 volt, 220 volt). In one embodiment, the temperature controller 66 may include a solid state relay. Based upon data communicated from the electronic interface device 68, the temperature controller 66 adjusts the electrical current communicated to the heating element 60 to raise and/or lower the temperature within the housing 12. Alternatively, to cool the gas chromatograph oven 10, the temperature controller 66 preferably communicates an electrical current which opens and/or closes a control valve 72, controlling the flow of liquid nitrogen into the housing 12 from the source 56 via the cooling port 54.

Figure 4:
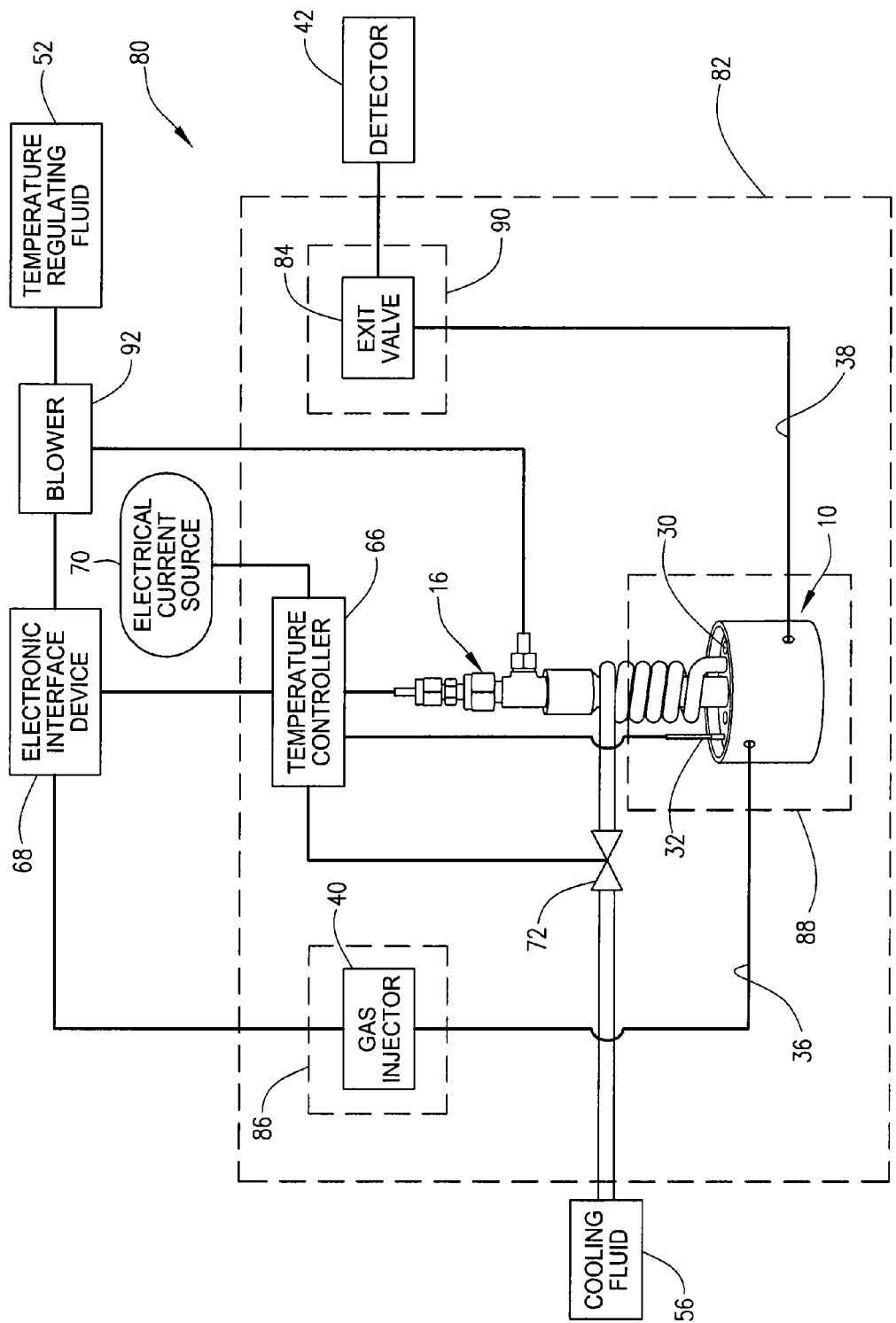
FIG. 4 is a schematic representation of a gas chromatograph device employing the gas chromatograph oven of the present invention.

Referring now to FIG. 4, shown is a gas chromatograph device 80 having the gas chromatograph oven 10. The gas chromatograph device 80 is shown as generally including a chromatograph housing 82, the gas injector 40, the gas chromatograph oven 10, an exit valve 84, and the gas detector 42. In general, the chromatograph housing 82 has three separated, insulated chambers 86, 88, 90 which each separately house the gas injector 40, the gas chromatograph oven 10, and the exit valve 84, respectively.

The gas injector 40 is shown as associated with the gas inlet end 36 of the gas chromatograph oven 10. The gas injector 40 is preferably controlled by the electronic interface device 68 and is configured to inject both a stationary phase material and test material into the gas chromatograph oven 10.

In accordance with the present disclosure, the gas chromatograph oven 10 is shown as associated with the temperature controller 66. The temperature controller 66 may preferably be at least partially positioned within the chromatograph housing 82.

The exit valve 84 (also known as a splitter valve) is shown as associated with the gas detector end 38. The exit valve 84 operates to control the amount of column material entering the gas detector 42. It will be appreciated by those of ordinary skill in the art that the use of the exit valve 84 does not need to be employed, and it may in fact be more desirable to omit the exit valve 84 to permit more column material to enter the gas detector 42.

To analyze a test material, the gas injector 40 injects a test material into the capillary column 34 via the gas inlet end 36. Next, the system heats the gas chromatograph oven 10 by communicating with the temperature controller 66 via the electronic interface device 68. This communication sends an electrical current to the heating element 60. Next, a blower 92 associated with the thermal control assembly 16 communicates forced air therethrough, passing air over the heating element 60. It will be appreciated that other means for conveying air through the thermal control assembly 16 may be used, such as the use of compressed air. This communication of air operates to heat the capillary tube receiving space 22 of the housing 12. Forced air is communicated out of the outlet ports 30 of the housing 12 to keep heated air continuously circulating within the housing 12. As the temperature increases inside the capillary column 34, the test material and the stationary phase material interact, separating the test material. Separated components leave the gas chromatograph oven 10 through the detector interface end 38 whereupon the separated test material is passed to the gas detector 42 for analysis.

To quickly cool the gas chromatograph oven 10 for rapid, successive and/or automated analyses of test materials, liquid nitrogen is communicated into the capillary tube receiving space 22 of housing 12 via the cooling port 54.

The chromatograph oven 10 of the present invention may also be used to retrofit existing gas chromatographs to enable them to be heated-up and cooled-down more quickly. Other advantageous of the small volume oven of the present invention include minimizing gas chromatograph size to simplify hyphenated analysis system connections; cryogenic focusing produces sharp peaks (e.g., two second baseline widths); wide range of column lengths can be employed; repetitive injection capabilities for process monitoring; and high heating rates with a low power heater (e.g., 200-1000 watts).

The invention will be more fully understood by reference to the following example. However, the example is merely intended to illustrate desirable aspects of the invention and is not to be construed to limit the scope of the invention.

EXAMPLE

Figure 5:
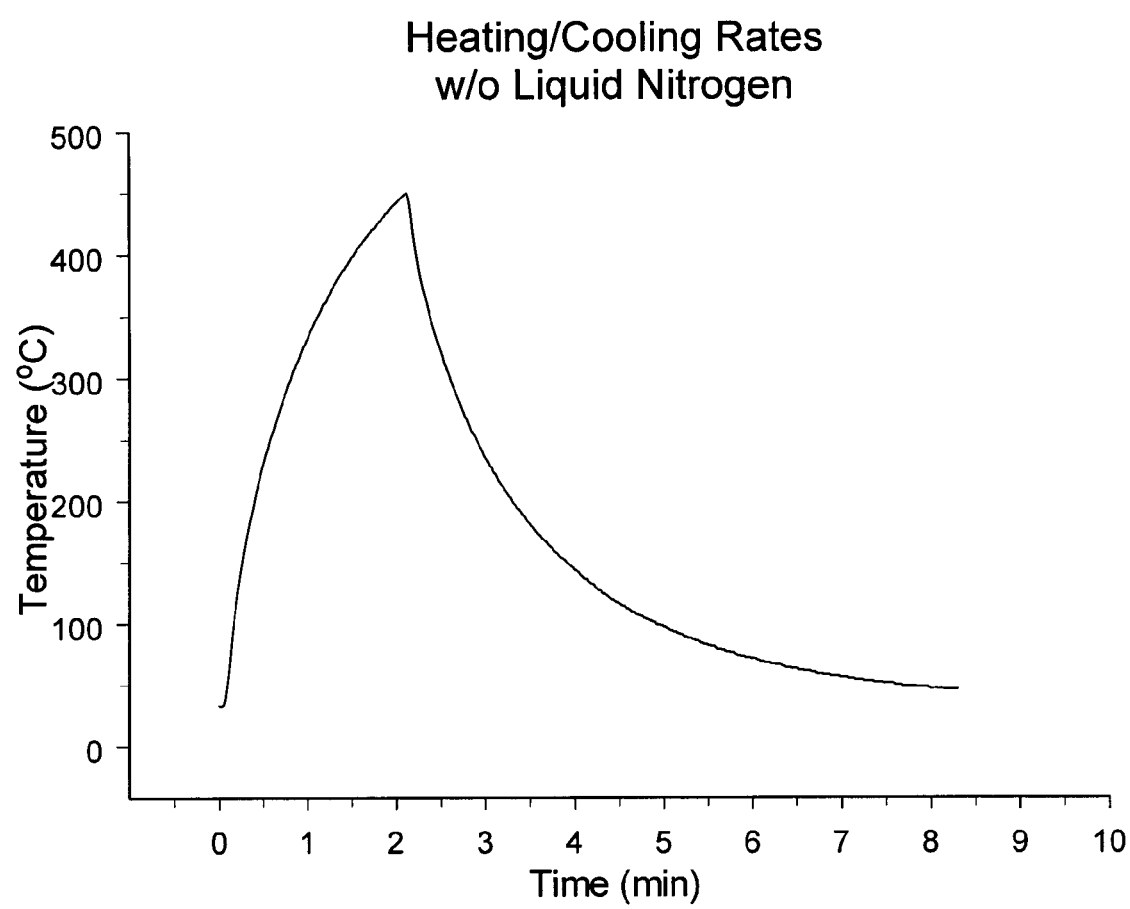
FIG. 5 is a graphical representation of a temperature versus time profile for heating and cooling the gas chromatograph oven without the use of liquid nitrogen.

A gas chromatograph oven was tested to evaluate its heating and cooling characteristics (25° C. ambient temperature). The graph depicted in FIG. 5 shows the results of using a 200 W heating element and turning the heater fully on until the temperature reached 450° C. At that point, the heater was turned off and the oven was allowed to cool. The oven heated to 450 C in 2.2 minutes. The average heating rate over this 425° C. temperature range was 3.2° C./second. The graph shows that the heating rate changed with time and was much higher than this average initially. The table below lists the average heating rates calculated for 50° C. intervals. After turning the heater off, the oven temperature dropped exponentially and reached 50° C. in 6.2 minutes.

| Temperature Range | Average Heating Rate (° C./second) |
|---|---|
| 33 to 100° C. | 6.9 |
| 100 to 150° C. | 8.3 |
| 150 to 200° C. | 5.9 |
| 200 to 250° C. | 4.7 |
| 250 to 300° C. | 3.5 |
| 300 to 350° C. | 2.7 |
| 350 to 400° C. | 2.0 |
| 400 to 450° C. | 1.4 |

Figure 6:
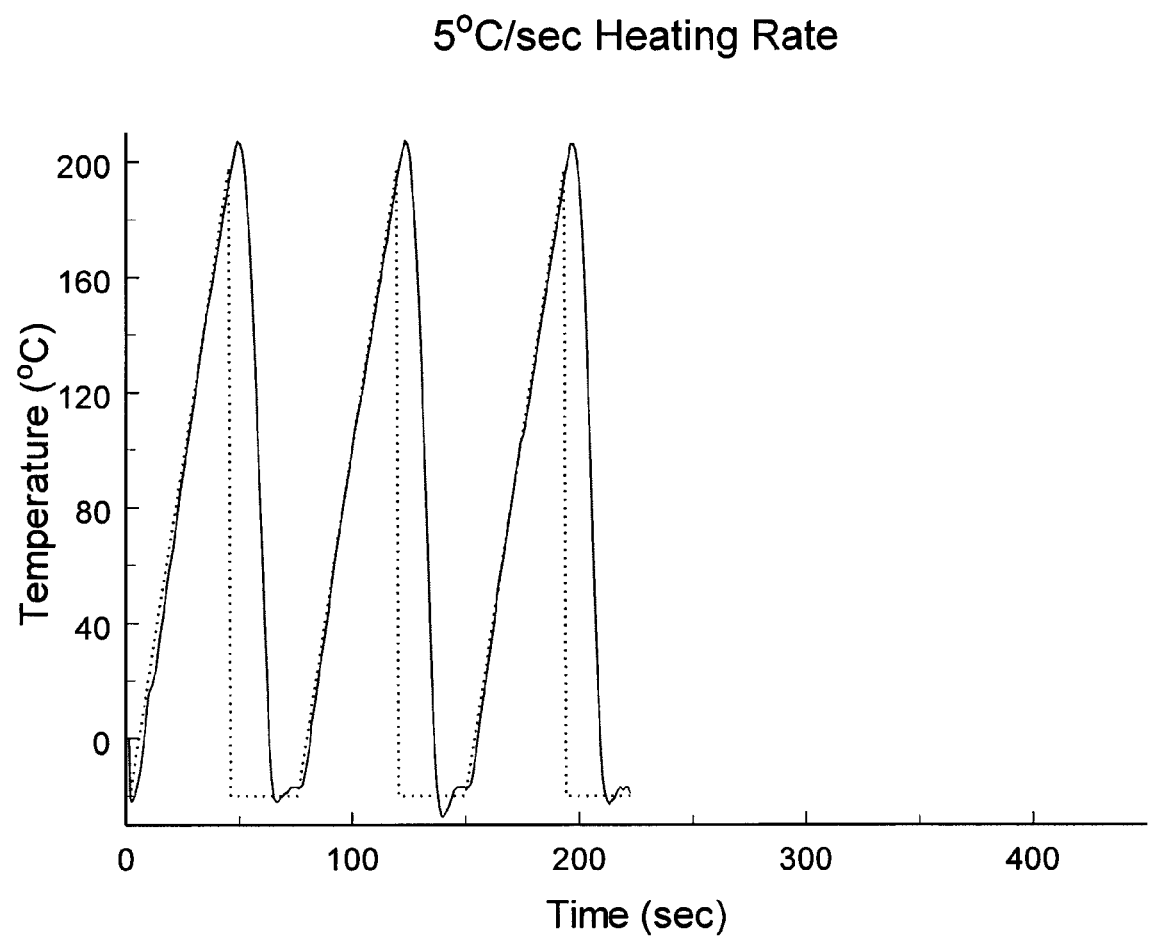
FIG. 6 is a graphical representation of a temperature ramp versus time profile for heating and cooling the gas chromatograph oven with the use of liquid nitrogen

The gas chromatograph oven was interfaced to a Hewlett Packard 5973 quadrupole mass spectrometer in order to facilitate gas chromatography/mass spectrometry (GC/MS) measurements. An Omega CN3202 temperature controller was employed to measure and adjust oven temperatures and to provide oven heating ramps for GC/MS measurements. Liquid nitrogen coolant was employed for cryogenic focusing (i.e., sub-ambient initial oven temperatures) and to rapidly cool the oven after each temperature ramp. FIG. 6 is a graph that shows a typical temperature ramp. A sample was injected into the capillary tube when the gas chromatograph oven temperature was minus 20° C. (time=zero minutes). The oven temperature was ramped to 200° C. in forty-four seconds (5° C./sec) to achieve separation of injected mixture components. After forty-four seconds, the oven temperature was decreased to minus 20° C. to prepare for another sample injection. This was done by allowing liquid nitrogen to enter the oven. A solenoid valve, which was activated by the temperature controller, was employed to turn on and off the liquid nitrogen flow. There is a reasonable match between the programmed heating ramp (dotted line) and the actual temperature profile. After forty-four seconds, the programmed profile (dotted line) shows an instantaneous step from 200° C. to −20° C. Although liquid nitrogen cooling was rapid, it was not instantaneous; therefore the two lines do not match well. The graph shows that liquid nitrogen cooling reduced the oven temperature from 200° C. to −20° C. in about fifteen seconds (~15E C/sec).

Figure 7:
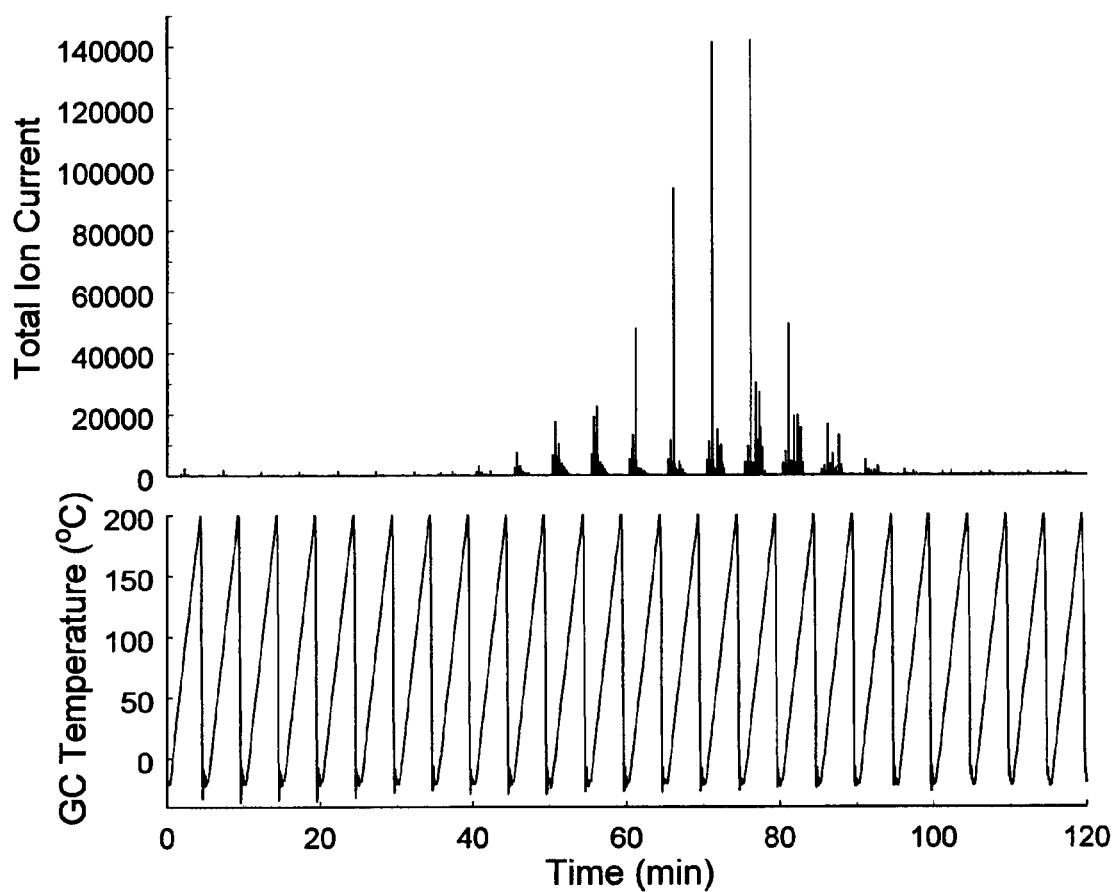
FIG. 7 is a graphical representation of a gas chromatogram versus time for a repetitive injection analysis and a graphical representation of oven temperature versus time for the repetitive injection analysis.

The GC/MS system incorporating the gas chromatograph oven was employed to monitor the composition of gases evolved while heating a polymer mixture in the presence of a solid acid catalyst. Volatile products were monitored to follow the thermal decomposition processes of the polymers that were catalyzed by the solid acid. The catalyst/polymer sample was heated in a furnace from 100° C. to 400° C. at a rate of 2.5° C./min. While heating, the evolved gases were sampled and analyzed by GC/MS every five minutes. By employing repetitive injection analysis, evolved gas mixture components were separated by the gas chromatograph oven and detected by the mass spectrometer. The resulting gas chromatograms (top) and corresponding gas chromatograph oven temperature profiles (bottom) are shown in FIG. 7.

Twenty-four successive evolved gas injections were made while heating the catalyst/polymer sample from 100° C. to 400° C. Evolved gases were analyzed at 12.5° C. intervals (i.e., every five minutes) during the catalyst/polymer heating experiment. Each five minutes measurement represents a discrete sampling of the gases evolved from the heated catalyst/polymer sample. Each vertical line in the mass spectrometer data denotes the presence of a distinct mixture component contained in the evolved gas. The height of each vertical line represents the abundance of that mixture component in the evolved gas.

Figure 8:
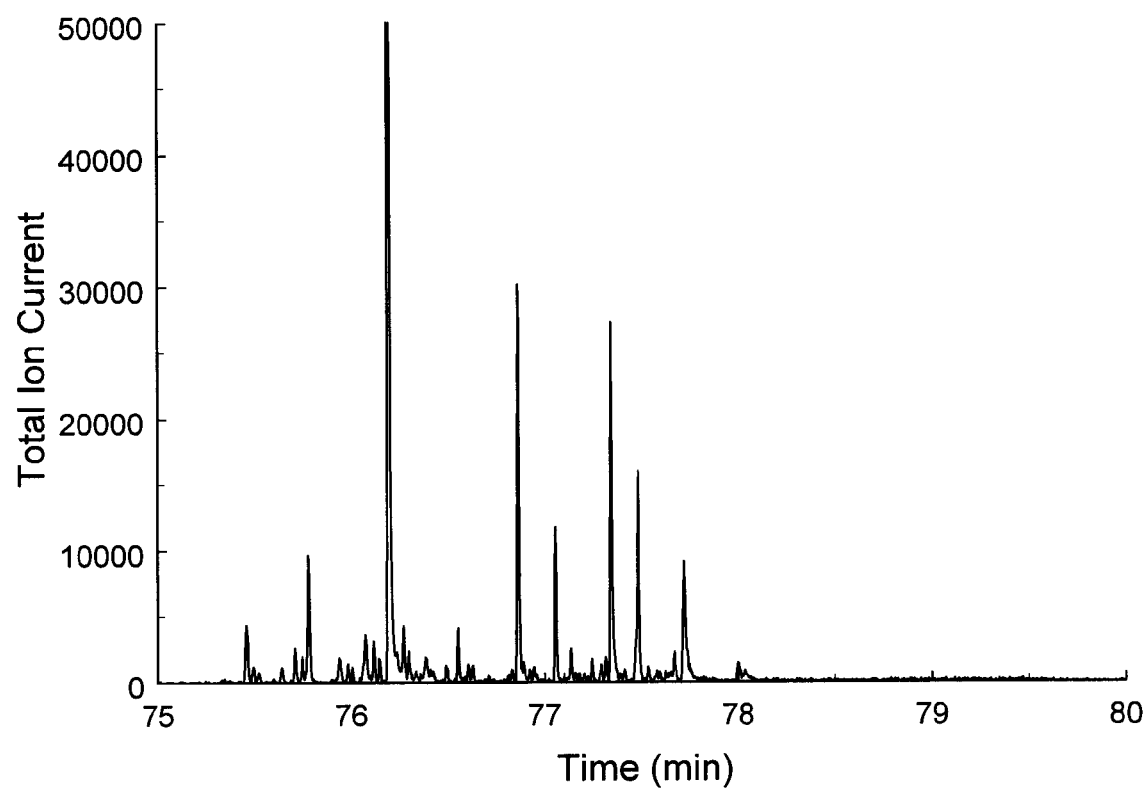
FIG. 8 is an enlarged graphical representation of the gas chromatogram obtained by injecting evolved gases into the gas chromatograph oven at the seventy-five minute mark of the chromatograms of FIG. 7.

FIG. 8 is a graph illustrating an enlarged view of the gas chromatogram obtained by injecting evolved gases into the gas chromatograph oven at the seventy-five minute mark. It can be seen that the lines in the plot above are actually peaks. Because of cryogenic focusing (i.e., starting at −20° C.), these peaks were narrow (about two seconds wide) and consequently mixture components were well separated from each other. At least thirty distinct peaks (mixture components) can be discerned in the acquired data.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A gas chromatograph oven, comprising:
a housing defining a capillary tube receiving space, the housing having at least one outlet port to permit the passage of a fluid from the capillary tube receiving space of the housing;
at least one capillary tube positioned in the capillary tube receiving space of the housing, the at least one capillary tube having a gas inlet end connectable to a gas injector and a gas detector end connectable to a gas detector; and
a thermal control assembly in fluid communication with the capillary tube receiving space of the housing, the thermal control assembly comprising a first tube having a heating element positioned therein and being connectable to a temperature regulating fluid source and a second tube connectable to a source of a cooling fluid;
wherein the first tube is positioned external to the housing and connected to the housing such that upon passing temperature regulating fluid through the first tube and over the heating element the temperature regulating fluid is heated and the heated fluid passes into the capillary receiving space where the heated fluid circulates about the at least one capillary tube and passes from the housing through the at least one outlet port; and
wherein the second tube is positioned external to the housing and connected to the housing such that cooling fluid is passed into the capillary receiving space upon passing the cooling fluid through the second tube where the cooling fluid circulates about the at least one capillary tube and passes from the housing through the at least one outlet port.

2. The gas chromatograph oven of claim 1, wherein the gas inlet end of the at least one capillary tube extends from the housing.

3. The gas chromatograph oven of claim 2, wherein the gas detector end of the at least one capillary tube extends from the housing.

4. The gas chromatograph oven of claim 1, wherein the housing includes a body member and a cap member, the cap member being selectively detachable from the body member.

5. The gas chromatograph oven of claim 1, wherein the at least one capillary tube has a coil, and wherein the housing is shaped to substantially conform to the shape of the coil.

6. The gas chromatograph oven of claim 5, wherein the coil has a diameter of about 1.5 inches.

7. The gas chromatograph oven of claim 1, wherein the second tube is coiled about at least a portion of the first tube.

8. The gas chromatograph oven of claim 1 further comprising a temperature controller associated with at least one of the heating element or the second tube.

9. The gas chromatograph oven of claim 8, wherein the temperature controller communicates electrical current to the heating element.

10. A gas chromatograph, comprising:
a gas chromatograph oven comprising:
a housing defining a capillary tube receiving space, the housing having at least one aperture to permit the passage of a fluid from the capillary tube receiving space of the housing;
at least one capillary tube positioned in the capillary tube receiving space of the housing, the at least one capillary tube having a gas inlet end and a gas detector end; and
a thermal control assembly in fluid communication with the capillary tube receiving space of the housing, the thermal control assembly connectable to a source of a temperature regulating fluid;
a gas injector in fluid communication with the gas inlet end of the at least one capillary tube;
a gas detector in fluid communication with the gas detector end of the at least one capillary tube;
a source of temperature regulating fluid connected to the thermal control assembly,
wherein the thermal control assembly comprises a tube positioned external to the housing, the tube having a resistive heating element positioned therein, and wherein the tube is in fluid communication with the source of temperature regulating fluid such that the temperature regulating fluid is heated upon passing through the tube.

11. The gas chromatograph of claim 10 further comprising a chromatograph housing having a first chamber and a second chamber wherein the gas injector is at least partially positioned within the first chamber of the chromatograph housing, and the gas chromatograph oven is at least partially positioned within the second chamber.

12. The gas chromatograph of claim 11, wherein the gas inlet end of the at least one capillary tube extends from the housing.

13. The gas chromatograph of claim 12, wherein the gas detector end of the at least one capillary tube extends from the housing.

14. The gas chromatograph of claim 11, wherein the at least one capillary tube has a coil, and wherein the housing of the gas chromatograph oven is shaped to substantially conform to the shape of the coil.

15. The gas chromatograph of claim 14, wherein the coil has a diameter of about 1.5 inches.

16. The gas chromatograph of claim 15, wherein the thermal control assembly further comprises a cooling port in fluid communication with the capillary tube receiving space of the housing and wherein the gas chromatograph further comprises a source of cooling fluid in fluid communication with the cooling port.

17. The gas chromatograph of claim 10, wherein the source of cooling fluid in fluid communication with the cooling port is liquid nitrogen.

18. The gas chromatograph of claim 17 further comprising a temperature controller associated with at least one of the heating element or the cooling port.

19. A method of subjecting a sample gas to rapid thermal cycling, the method comprising:
injecting a sample gas into a coiled capillary tube positioned within a housing, the housing having at least one outlet port to permit the passage of fluid from the capillary tube receiving space;
passing a heated fluid into and out of the housing such that the heated fluid is in direct thermal communication with the coiled capillary tube thereby raising the temperature within the housing to a predetermined upper temperature so as to cause the sample gas to separate into separated components;
detecting the separated components of the sample gas;
terminating passage of the heated fluid; and
passing a cooling fluid into and out of the housing such that the cooling fluid is in direct thermal communication with the coiled capillary tube thereby lowering the temperature of the coiled capillary tube to a predetermined lower temperature.

20. A method of subjecting a sample gas to rapid thermal cycling, the method comprising:
circulating a cooling fluid through a housing having a coiled capillary tube positioned therein such that the cooling fluid is in direct thermal communication with the coiled capillary tube thereby lowering the temperature of the coiled capillary tube to a predetermined lower temperature which is less than ambient temperature;
subsequently injecting a sample gas into the coiled capillary tube positioned within a the housing;
circulating a heated fluid through the housing such that the heated fluid is in direct thermal communication with the coiled capillary tube thereby raising the temperature within the housing to a predetermined upper temperature so as to cause the sample gas to separate into separated components;

detecting the separated components of the sample gas; and
terminating circulation of the heated fluid.

21. The method of claim 20 further comprising the step of:
circulating the cooling fluid through the housing subsequent to terminating circulation of the heated fluid to lower the temperature of the coiled capillary tube to the predetermined lower temperature.

* * * * *

UNITED STATES PATENT AND TRADEMARK OFFICE
CERTIFICATE OF CORRECTION

PATENT NO. : 7,984,638 B2  Page 1 of 1
APPLICATION NO. : 12/167483
DATED : July 26, 2011
INVENTOR(S) : White It is certified that error appears in the above-identified patent and that said Letters Patent is hereby corrected as shown below:

In the Claims:
Column 9, line 5: After "within" delete "a"

Signed and Sealed this
Twenty-seventh Day of September, 2011

David J. Kappos
*Director of the United States Patent and Trademark Office*